US010885646B2

(12) United States Patent
Holmes (10) Patent No.: US 10,885,646 B2
(45) Date of Patent: Jan. 5, 2021

(54) COMPENSATING OPTICAL COHERENCE TOMOGRAPHY SCANS

(71) Applicant: Michelson Diagnostics Ltd., Maidstone (GB)

(72) Inventor: Jonathan Denis Holmes, West Maling (GB)

(73) Assignee: Michelson Diagnostics Ltd., Maidstone (GB)

(*) Notice: Subject to any disclaimer, the term of this patent is extended or adjusted under 35 U.S.C. 154(b) by 71 days.

(21) Appl. No.: 16/093,307

(22) PCT Filed: Apr. 20, 2017

(86) PCT No.: PCT/GB2017/051108
§ 371 (c)(1),
(2) Date: Oct. 12, 2018

(87) PCT Pub. No.: WO2017/182816
PCT Pub. Date: Oct. 26, 2017

(65) Prior Publication Data
US 2020/0027227 A1    Jan. 23, 2020

(30) Foreign Application Priority Data

Apr. 20, 2016    (GB) .................................. 1606897.5

(51) Int. Cl.
*G06T 7/521*    (2017.01)
*A61B 5/00*    (2006.01)
(Continued)

(52) U.S. Cl.
CPC ............ *G06T 7/521* (2017.01); *A61B 5/0033* (2013.01); *A61B 5/0066* (2013.01); *G06T 5/002* (2013.01);
(Continued)

(58) Field of Classification Search
None
See application file for complete search history.

(56) References Cited

U.S. PATENT DOCUMENTS

2013/0095519 A1* 4/2013 Backman ............ A61B 5/0066
435/34
2014/0099011 A1    4/2014 Begin
(Continued)

FOREIGN PATENT DOCUMENTS

| EP | 2884223 A1 | 6/2015 |
| WO | 99/25249 A1 | 5/1999 |
| WO | 2012/170722 A2 | 12/2012 |

OTHER PUBLICATIONS

International Search Report dated Jul. 26, 2017 for International Application No. PCT/GB2017/051108.
(Continued)

*Primary Examiner* — Leon Viet Q Nguyen
(74) *Attorney, Agent, or Firm* — Burns & Levinson LLP; Steven M. Mills (57) ABSTRACT

A method of processing optical coherence tomography (OCT) scans, comprising: receiving OCT data comprising an OCT signal indicative of the level of scattering in a sample, the OCT data including the OCT signal for at least one scan through the sample, with the OCT signal having been measured at varying depth and position through the sample in each scan; processing the OCT data for each scan with depth to produce a indicative depth scan representative of the OCT signal at each depth through all of the scans; fitting a curve to the indicative depth scan, the curve comprising a first term which exponentially decays with respect to the depth and a second term which depends on the noise in the OCT signal; and calculating a compensated intensity for the OCT signal at each point through each scan, the compensated intensity comprising a ratio of a term
(Continued)

comprising a logarithm of the OCT signal to a term comprising the logarithm of the fitted curve.

22 Claims, 7 Drawing Sheets

(51) Int. Cl.
  *G06T 5/00* (2006.01)
  *G06T 7/00* (2017.01)
(52) U.S. Cl.
  CPC .. *G06T 7/0012* (2013.01); *G06T 2207/30041* (2013.01); *G06T 2207/30088* (2013.01); *G06T 2210/41* (2013.01)

(56) References Cited

U.S. PATENT DOCUMENTS

| | | | |
|---|---|---|---|
| 2014/0355586 A1 | 12/2014 | Wang et al. | |
| 2014/0355856 A1* | 12/2014 | Wang | G06T 11/005 382/131 |
| 2016/0317020 A1* | 11/2016 | Liu | G01B 9/02076 |

OTHER PUBLICATIONS

Search Report under Section 17 dated Feb. 22, 2017 for Great Britain Application No. 1606897.5.
Kim, Keo-Sik et al. Enhanced optical coherence tomography imaging using a histogram-based denoising algorithm. Optical Engineering 54(11), p. 113110 (Nov. 25, 2015).

\* cited by examiner

COMPENSATING OPTICAL COHERENCE TOMOGRAPHY SCANS

CROSS-REFERENCE TO RELATED APPLICATIONS

This application is the U.S. national phase entry under 35 U.S.C. § 371 of International Application No. PCT/GB2017/051108, filed Apr. 20, 2017, entitled COMPENSATING OPTICAL COHERENCE TOMOGRAPHY SCANS, which in turn claims priority to and benefit of Great Britain Patent Application No. 1606897.5, filed Apr. 20, 2016, the contents of which are incorporated herein by reference in their entirety for all purposes.

FIELD

This invention relates to methods of processing optical coherence tomography (OCT) scans, and to related apparatus.

BACKGROUND

Optical Coherence Tomography (OCT) was invented in 1991 at MIT in the USA and is commonly used for imaging human tissue of various organs, in particular the eye, and also skin (J. Welzel, "Optical coherence tomography in dermatology: a review," *Skin Research and Technology*, vol. 7, pp. 1-9. 2001).

Those skilled in the art will be familiar with the VivoSight OCT device, manufactured and marketed by Michelson Diagnostics Ltd of Maidstone, Kent, United Kingdom, which is designed for use by professional dermatologists in the assessment of skin lesions of patients. The VivoSight OCT device scans the skin and presents to the user images of the skin subsurface structure, in a plane perpendicular to the skin surface. This is known as a 'B-scan'.

Also, VivoSight can acquire scans at multiple locations across the skin surface in order to build up a series of B-scans across a lesion of interest. This is known as a multi-slice 'stack' and can be viewed by the user in a variety of ways to elicit tissue features of medical interest such as nests of cancer cells. For example, the user can view the stack of B-scans in rapid succession to 'fly through' the lesion area.

The OCT signal is obtained from the optical scattering from tissue illuminated by a scanned laser beam. Only the light that is scattered back towards the illumination direction is collected and analysed. Due to the optical scattering properties of tissue, the magnitude of the OCT signal falls off exponentially with depth into the tissue. In order to produce a usable OCT image, by convention a logarithm of the OCT intensity is calculated, such that the displayed grey-level intensity is proportional to the logarithm of the OCT signal plus an offset.

$$\text{OCT signal} = Ae^{-\alpha z}$$

$$\log(\text{OCT signal}) = A - \alpha z$$

$$\text{Displayed intensity} = I_0(\log(\text{OCT signal}) - w_0)$$

Where $\alpha$ is the 'optical attenuation coefficient' of the tissue, z is the depth below the surface of the tissue, and A is a constant that depends upon the sensitivity of the OCT device, and $I_0$ and $w_0$ are constants that depend on the characteristics of the display, chosen such that the maximum displayed intensity of a typical sample is close to the maximum displayable intensity, and such that the displayed intensity at large depths (where the OCT signal is small compared to noise) is close to the minimum displayable intensity.

This means that a target with a constant 'optical attenuation coefficient' $\alpha$ will be displayed with a linear reduction in grey level intensity with depth. In general, this method produces acceptable images and is the accepted standard approach to displaying OCT data.

However, this method has some practical drawbacks. One problem is that the image becomes progressively dimmer with depth, and so it can be difficult to visually make out clinically important details in the image that are in the lower, deeper portion of the skin. Some attempts have been made to compensate for this (Ali Hojjatoleslami and Mohammad R. N. Avanaki, "OCT skin image enhancement through attenuation compensation," Appl. Opt. 51, 4927-4935 (2012)) by artificially boosting the displayed intensity for deeper regions of the tissue, in proportion to the calculated attenuation by tissue in the shallower regions. However, a problem with this approach is that there is also a contribution to the OCT signal from noise, which may arise from multiple sources such as optical noise in the laser or noise in the detector or detection electronics. In the deeper portion of the image where the signal has been artificially boosted, the noise is likewise boosted, resulting in an image that is visually unappealing and difficult to use, and this approach has not found favour.

Another problem is that the magnitude of the OCT signal depends upon the distance of the sample from or to the probe. This means that in an OCT system where the probe-to-sample distance can vary for practical reasons, the brightness of the image of the sample will also vary. There are at least two reasons why the magnitude of the OCT signal may vary in this way. One reason is the limited coherence length of the laser. The coherence of the laser light falls with distance from the interference 'match point' which is usually positioned at the top of the OCT frame, producing a corresponding loss in interference, which is the source of the OCT signal. In simple terms, the image becomes dimmer, the lower the sample appears in the image frame. A second reason is the limited depth of focus of the imaging optics. When the laser beam is tightly focussed, the resulting OCT signal is strong, but away from the focal plane, the laser beam is spread over a broad area and the resulting OCT signal is weakened. So this means that the OCT image appears brightest when the sample is located within the in-focus depth range.

Figure 1:
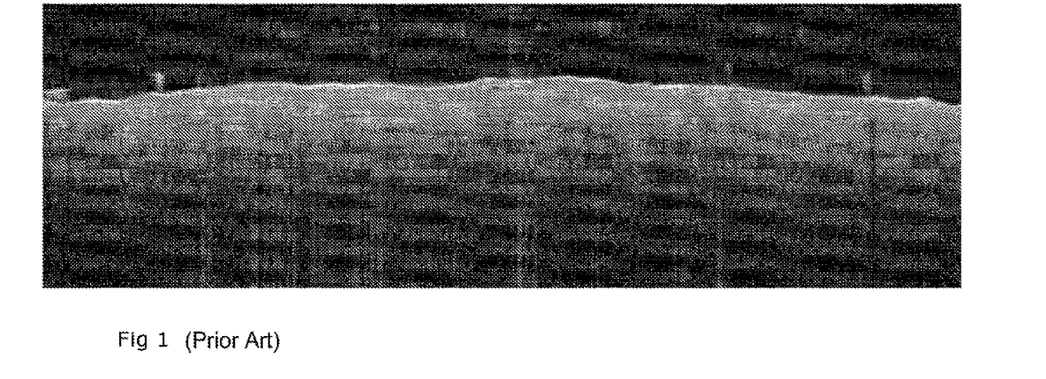
FIG. 1 shows an OCT scan depicted in accordance with a prior art method.
Figure 2:
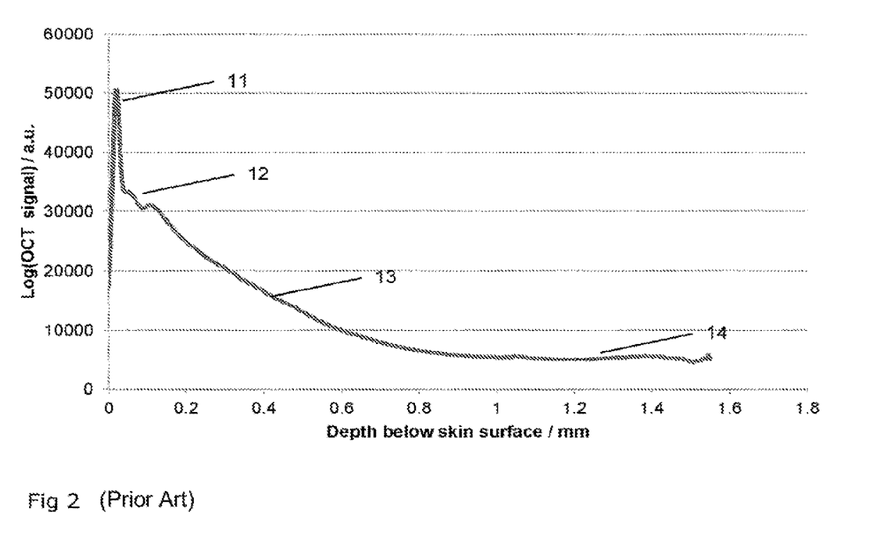
FIG. 2 shows a graph of OCT intensity with depth in a sample of skin.

FIG. 1 of the accompanying drawings shows an example OCT image of skin using the conventional logarithm of OCT signal; FIG. 2 of the accompanying drawings shows the intensity fall-off with depth for this image; and FIG. 3 of the accompanying drawings shows the corresponding OCT image with the logarithmed OCT signal artificially boosted in proportion to the calculated attenuation with depth. None of these images is entirely satisfactory.

BRIEF SUMMARY

According to a first aspect of the invention, there is provided a method of processing optical coherence tomography (OCT) scans, comprising:
receiving OCT data comprising an OCT signal indicative of the level of scattering in a sample, the OCT data including the OCT signal for at least one scan through the sample, with the OCT signal having been measured at varying depth and position through the sample in each scan;

processing the OCT data for each scan with depth to produce a indicative depth scan representative of the OCT signal at each depth through all of the scans;

fitting a curve to the indicative depth scan, the curve comprising a first term which exponentially decays with respect to the depth and a second term which depends on the noise in the OCT signal; and calculating a compensated intensity for the OCT signal at each point through each scan, the compensated intensity comprising a ratio of a term comprising a logarithm of the OCT signal to a term comprising the fitted curve.

The compensated intensity can then be displayed to the user by generating an image in which each pixel of the image is displayed at an intensity indicated by the compensated intensity, typically modified by the application of a multiplicative scale factor and an additive offset.

We have found that such a display enhances the visibility to the user of sample features that are at large depths and reduces the visible effects of noise on OCT signals at high depth through the sample. There may be a single scan, or a plurality.

Typically, each scan will represent a slice through the sample having varying depth and position perpendicular to the depth in a single direction, commonly known as a B-scan.

The method may comprise determining the position of the surface of the sample within each scan, and measuring the depth from the surface. The determination of the surface of the sample may comprise a detection of the surface within the scan, or by inferring the position of the surface from the arrangement of the OCT apparatus which captured the OCT scans. The step of determining the position of the surface of the sample within each scan may comprise detecting the highest point at which there is a sudden large change in OCT signal intensity with depth, at each horizontal position in the scan, and then optionally calculating the average height of all such points.

The method may comprise the step of correcting the OCT data dependent on the distance the height of the surface of the sample in the OCT scans. In one embodiment, the OCT data will be corrected by applying an additive term, typically small, which depends upon height of the surface of the sample in the OCT scans. This additive term corrects for both the effect of the limited coherence length of the laser and the effect of the limited depth of focus of the probe. Typically, this additive term may be read out from a look-up-table previously produced by calibrating such effect variation with distance using a standard sample, or it can be calculated or fitted to a formula.

The indicative depth scan may represent the OCT signal at any given depth (typically within the sample), and as such may represent the mean A-scan taken through the sample, typically corrected to the depth of the sample surface. The processing may comprise detecting the surface position of the sample at each z location across the scan, offsetting the image data vertically by an amount equal to the surface position, so that the image pixels vertical position depends on depth below the sample surface, and averaging all image pixels at each depth. Alternatively or additionally, the processing may comprise using a filter such as a Kalman filter or Median filter.

The first and second terms may be additively combined. Typically, the fitted curve will be of the form:

$$f(z)=\log(Ae^{-\alpha z}+N)$$

where A, α and N are all constants to be determined when fitting the curve, and z is the depth through the sample. Conveniently, this provides the overall optical attenuation coefficient of the sample, α, and the background noise floor of the OCT device, N.

The step of fitting the curve may comprise an iterative method, such as an iterative hill descent curve fitting algorithm.

The term comprising the fitted curve may comprise a roll-off factor which varies the amount by which the compensation is reduced with increasing depth, in order to provide the best visual trade-off between increasing depth and increasing noise at large depths. Typically, this is a user-set parameter.

The compensated intensity may be calculated as:

$$\text{compensated intensity} = \frac{(\log(OCT \text{ signal}) - f_\infty)}{(r + f(z) - f_\infty)}$$

where f(z) is the fitted curve, r is the roll-off factor, and f∞ is the value of f(z) for large depths z (which is the background noise level). In essence, the amount of compensation with depth is rolled off smoothly as the noise contribution increases and becomes dominant, so that the resulting image does not show excessive noise at increased depths.

The resultant image may be filtered, typically to remove graininess due to noise. The filtering may be such that a degree of filtering increases with depth. This allows fine detail in the less deep parts of the image to be unaffected, whilst heavier filtering is applied in the deeper parts of the image where there is little fine detail. The filtering may comprise the application of at least one of a despeckle filter and a bilateral filter. The method may also comprise blending the effects of these two filters in a ratio that depends on depth.

Whilst the compensated display intensity in effect defines a grayscale image, the method may also comprise applying colour to the image. Typically, the colour applied to a pixel will depend on the difference between the compensated display intensity and the compensated fitted curve. In one embodiment, the colour applied to each pixel will have a hue which increases with increasing difference, and may be proportional thereto.

The method may comprise displaying the image on a display. The method may also comprise capturing the scans with an OCT apparatus.

Typically, the sample will be skin, retinal tissue, or anything else that can be visualised through OCT.

In accordance with a second aspect of the invention, there is provided an optical coherence tomography (OCT) image processing apparatus, comprising a processor, a display coupled to the processor and storage coupled to the processor, the storage carrying program instructions which, when executed on the processor, cause it to carry out the method of the first aspect of the invention.

The image processing apparatus may comprise an OCT apparatus by means of which the OCT scans are captured. As such, the image processing apparatus may comprise an OCT probe arranged to generated interferograms, and the processor may be arranged to generate the images from the interferograms. As such, the image processor may be arranged to process the images as they are captured.

Alternatively, the image processing apparatus may be separate from any OCT apparatus and may be arranged to process the images subsequent to their capture. As such the image processing apparatus may comprise data reception means (such as a network connection or media drive) arranged to receive the images for processing.

BRIEF DESCRIPTION OF THE DRAWINGS

There now follows, by way of example only, description of embodiments of the invention, described with reference to the accompanying drawings, in which.

DETAILED DESCRIPTION

Figure 4:
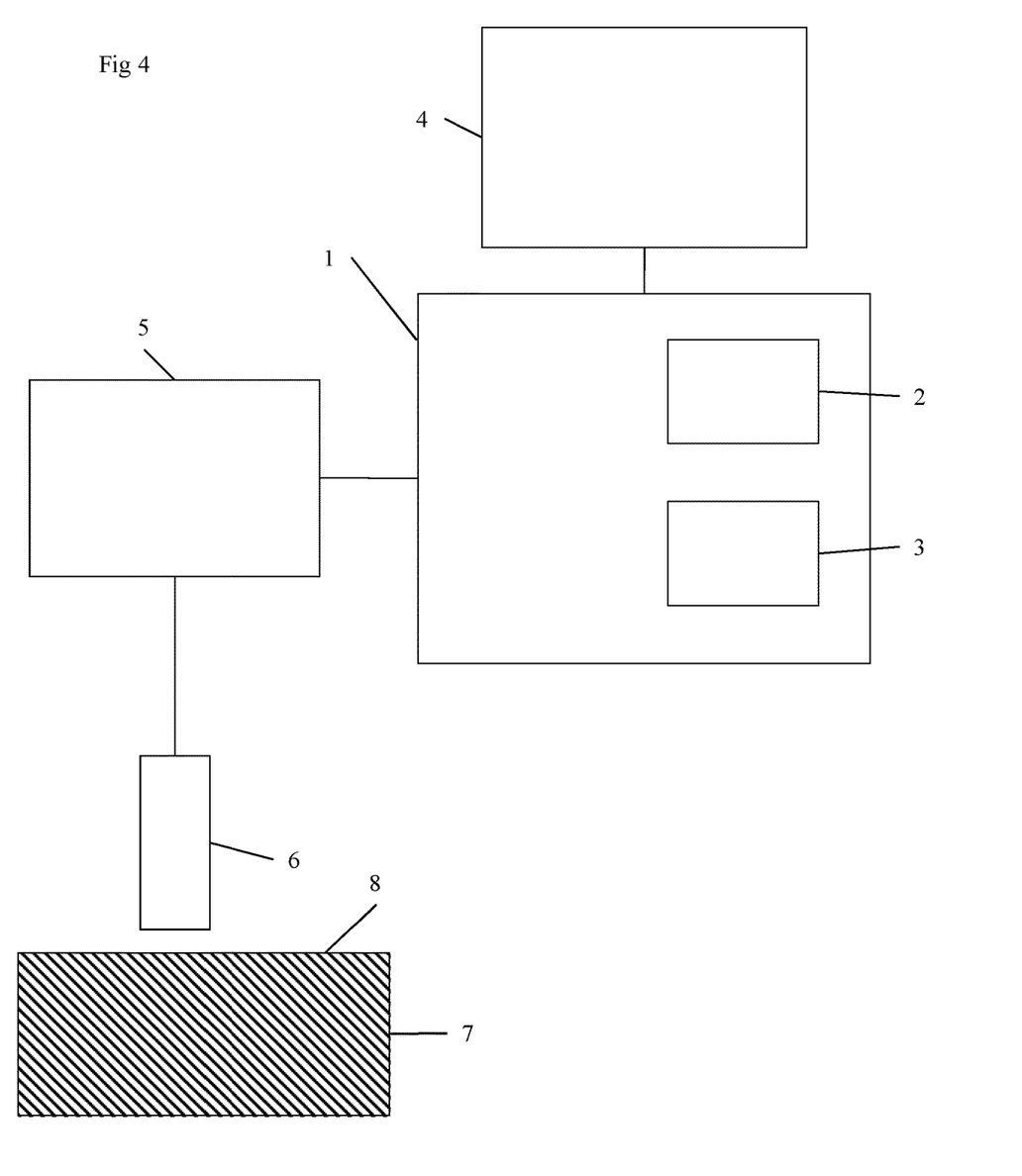
FIG. 4 shows schematically an optical coherence tomography (OCT) apparatus in accordance with an embodiment of the invention.

An optical coherence tomography (OCT) apparatus in accordance with an embodiment of the invention is shown in FIG. 4 of the accompanying drawings. This comprises a computer 1, having a processor 2 and storage 3 (such as a mass storage device or random access memory) coupled to the processor 2. The storage 3 contains data and processor instructions which cause the processor 2 to act as is described below. The computer 1 can be any suitable model; typically a personal computer running an operating system such as Microsoft® Windows® or Apple® Mac OS X® can be used. The computer 1 is also provided with a display 4 controlled by the processor 2 on which any desired graphics can be displayed.

The apparatus further comprises an OCT interferometer 5 and associated probe 6. The interferometer 5 interferes light reflected from sample 7 (here, a subject's skin) through probe 6 with light passed along a reference path to generate interferograms. These are detected in the interferometer 5; the measured signal is then passed to the computer 1 for processing. Example embodiments of suitable OCT apparatus can be found in the PCT patent application published as WO2006/054116 or in the VivoSight® apparatus available from Michelson Diagnostics of Maidstone, Kent, United Kingdom.

Such OCT apparatus typically generate multiple B-scans: that is, scans taken perpendicularly through the skin 7. The result of analysis of each interferogram is a bitmap in which the width of the image corresponds to a direction generally parallel to the skin surface and the height corresponds to the depth from the sensor into the skin. By taking many parallel scans, a three-dimensional stack of bitmaps can be built up.

The processor can then be used to process the OCT scans taken. The top surface of the sample 7 is determined, using the method disclosed in our previous PCT patent application published as WO2015/001317, although the surface of the sample 7 may also be estimated from the apparatus arrangement when in contact with the sample 7.

Figure 10:
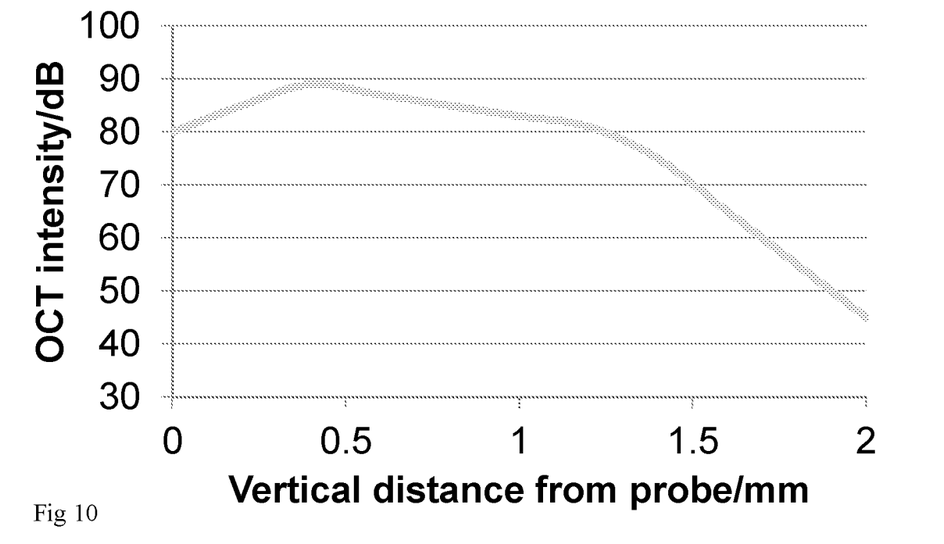
FIG. 10 shows a graph of OCT signal intensity with depth from the probe.
Figure 11:
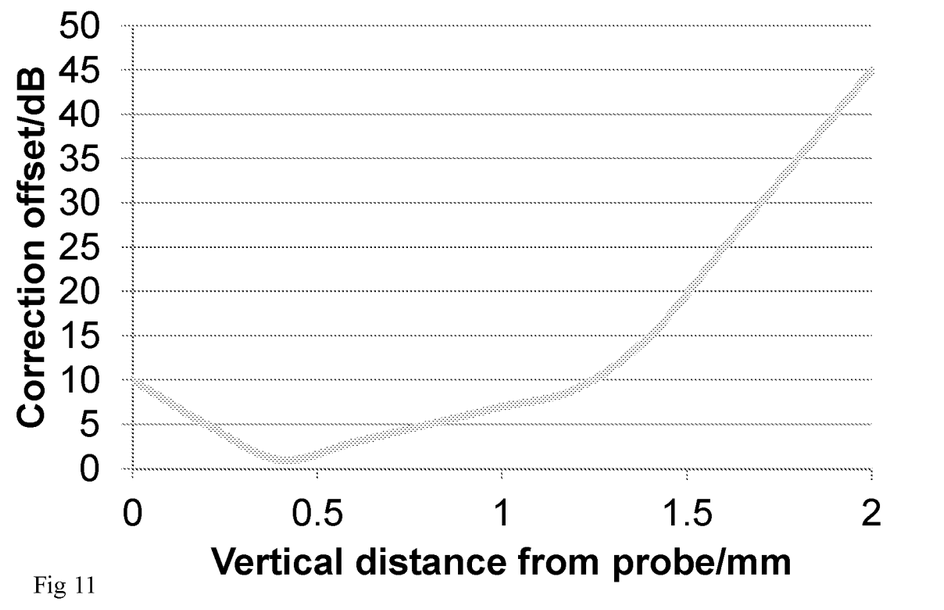
FIG. 11 shows a graph of a correction amount to correct for the effects of FIG. 10.

Having obtained the tissue surface, the entire data set is then corrected by adding an intensity offset to all sample pixels which is dependent upon the average distance of the tissue surface from the top of the image frame, using a predetermined lookup table. FIG. 10 of the accompanying drawings shows an example graph showing how the OCT signal intensity, measured in dB, varies with distance from the top of the image frame, determined experimentally. The signal falls overall as the distance increases, due to the fall of coherence of the laser, but there is also a region between 0.4 m and 1.4 mm where the signal is higher because this is the depth range where the beam is best focused. From this, a look-up table of offset values for each distance can be calculated by subtracting the measured OCT signal intensity from a maximum; an example look-up table depicted graphically is shown in FIG. 11 of the accompanying drawings. Thus, the average distance of the sample is looked up in the table to find an offset value to add to the entire OCT signal dataset of the sample.

Then, the entire data set is then analysed to obtain a mean intensity versus depth curve (as shown in FIG. 2), termed 'the mean A-scan'. Note that the intensity does not fall off perfectly linearly with depth; there is an initial 'spike' 11 which is caused by the specular reflection from the top surface; then an initial trough 12 which is due to the epidermis, which is known to be less scattering than the dermis, then an approximately linearly decreasing region 13 which is the upper dermis, and then a region 14 with smooth roll-off in the region where noise is significant and then dominant.

The OCT signal is modelled as comprising a component that falls off exponentially with depth (the desired signal from the tissue) and a component that is constant (i.e. the noise):

$$\text{OCT signal} = Ae^{-\alpha x} + \text{Noise}$$

Figure 5:
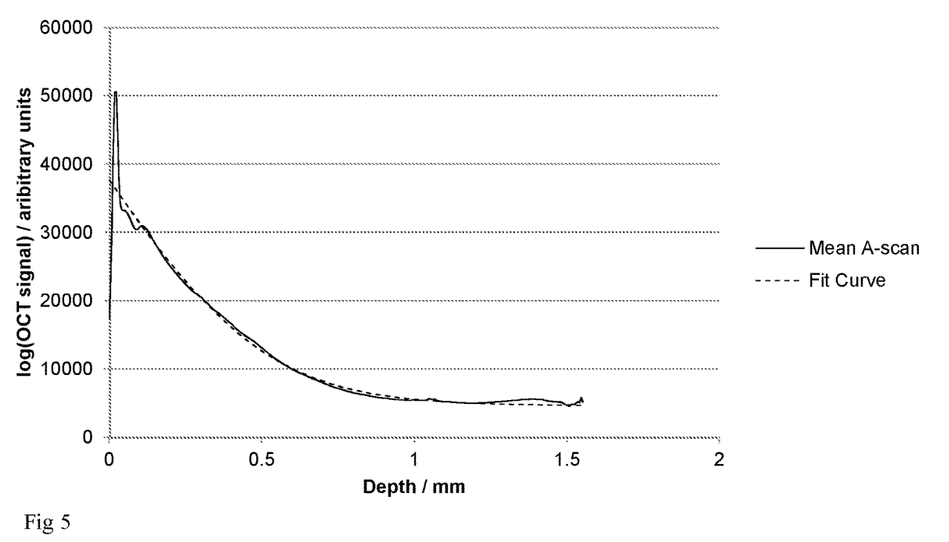
FIG. 5 shows a graph of the OCT signal and a curve fitted thereto with depth through the sample.

The logarithm of this equation is then fitted to the 'mean A-scan', such that the slope of the curve closely follows the mean A-scan in the area of the upper dermis, and then matches the roll-off into the depth region where noise dominates, as shown in FIG. 5 of the accompanying drawings. For example this fit is done with an iterative hill-descent curve fitting algorithm, but other algorithms may be used. The fitted curve is also offset so that at large depths it goes asymptotically to the background noise level.

This fitting process produces two useful parameters, which are the optical attenuation coefficient of the dermis a, and the magnitude of the noise. The figure a may be usefully output to the user as it may have clinical diagnostic value. The asymptotic magnitude of the OCT signal at large depths f∞ is measured, and may also be usefully output to the user as an indication of the OCT system sensitivity.

A depth-compensated image is then calculated by multiplying the logarithm of the OCT signal with a compensation function that varies with depth. This compensation function is:

$$\text{compensated intensity} = \frac{(\log(OCT\ \text{signal}) - f_\infty)}{(r + f(z) - f_\infty)}$$

In essence, the amount of compensation with depth is rolled off smoothly with a strength r as the noise contribution increases and becomes dominant, so that the resulting image does not show excessive noise at increased depths. Variations on this algorithm to produce the same result are possible.

Figure 6:
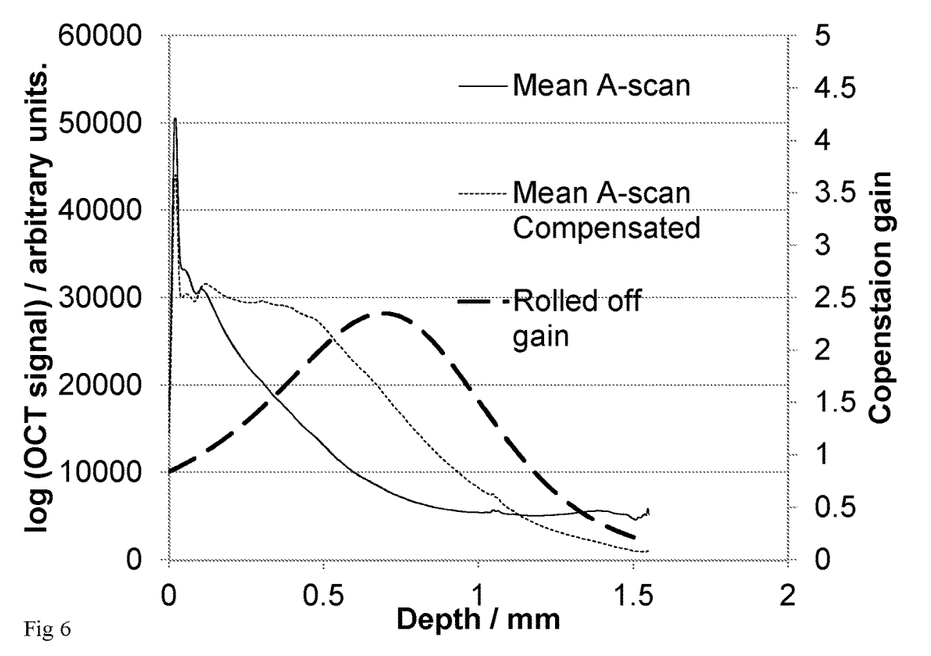
FIG. 6 shows a graph of the compensated OCT signal against depth, along with the degree to which the compensation is rolled off.
Figure 7:
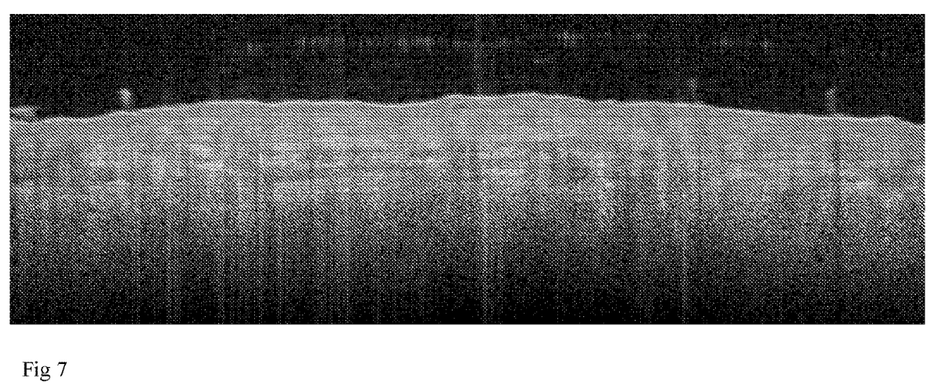
FIGS. 7, 8, 9a and 9b shows the same OCT scan as FIG. 2 compensated by the apparatus of FIG. 4 operating to three different methods, with FIGS. 9a and 9b showing the same image but shaded to indicate colour and in greyscale respectively.

FIG. 6 of the accompanying drawings shows the mean A-scan, the fitted curve f(z), the compensation function and the compensated A-scan. FIG. 7 of the accompanying drawings shows a compensated OCT image. By comparison with FIG. 1, it will be seen that the compensated image reveals more detail in deeper portions of the image.

Figure 3:
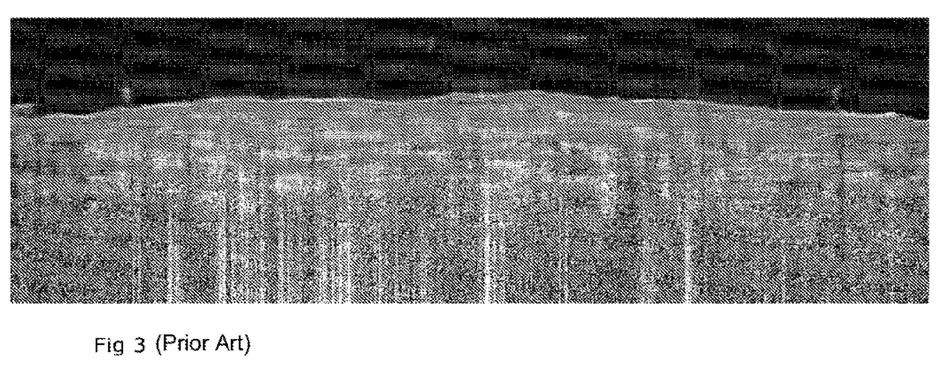
FIG. 3 shows the same OCT scan as FIG. 2 depicted in accordance with a different prior art method.

However, although a major improvement on FIG. 3, this compensated image still has an undesirable grainy texture in the lower portion of the image which is a result of the noise contribution. In a further improvement, the image can be filtered to reduce this graininess. The filtering is chosen such that the degree of filtering increases with depth, so that fine detail in the upper part of the image is unaffected, whereas heavier filtering is applied in the lower portion of the image where there is little fine detail. There are many possible filtering algorithms to achieve this result. One method is to apply a despeckle filter, and also a bilateral filter, and blending these results in a ratio that depends on the depth by applying a weighted average of the two, the weight being a linear function of depth going from 0 at or near the surface ($z_{min}$) and 1 at user-set depth $z_{max}$, as follows:

Call the first (despeckled) image D(z) and the second (bilateral filtered) image B(z); Set the depth range over which these are blended as $z_{min}$ and $z_{max}$;

Then the blending function g(z) is:

$$\begin{cases} 0 & \text{for } z \leq z_{min}; \\ (z - z_{min})/(z_{max} - z_{min}) & \text{for } z_{min} < z < z_{max}; \\ 1 & \text{for } z \geq z_{max} \end{cases}$$

Then the blended image is given by:

Blended intensity=$D(z) \cdot g(z) + B(z) \cdot (1-g(z))$

Figure 8:
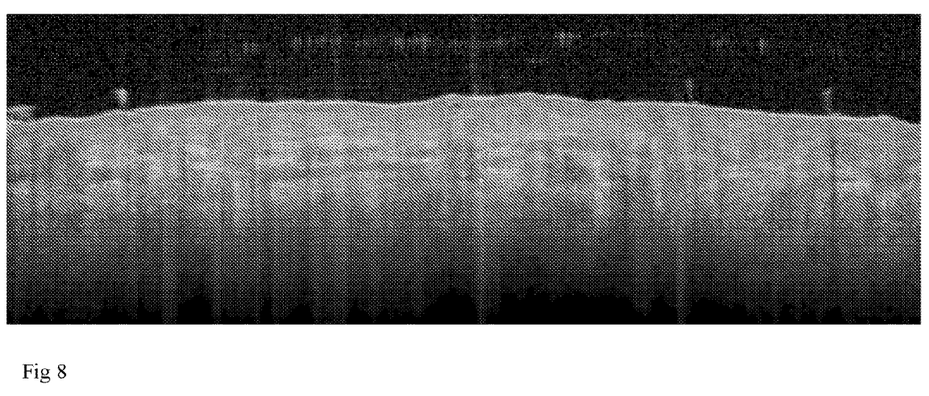

FIG. 8 of the accompanying drawings shows a compensated image that has been filtered in this manner. It will be seen that the grainy texture of the lower portion of the image has been eliminated and the result is more pleasing to the eye.

Finally, a scaling constant $I_0$ and offset is chosen such that the maximum OCT signal (typically at depth z=0) is displayed on the display device at an acceptably bright display intensity level.

Displayed intensity=$I_0(\log(OCT\ \text{signal}) - w_0)$

Here, $w_0$ corresponds to log(OCT signal) when the OCT signal is at or just above the noise floor f∞, and $I_0$ corresponds to ($I_{max}$/log(OCT signal)-$w_0$), when the OCT signal is the maximum observed, where $I_{max}$ is the maximum displayable intensity for the display device. These scaling and offset values may also be fine-tuned by trial and error from these starting values in order to arrive at a displayed image of most pleasing and clinically informative for typical samples, but will then be fixed.

For example, the typical maximum OCT signal may be +100 dB and the noise floor 15 dB, and the 16-bit display may output grey-level pixel intensities between 0 and 65,536. Then w0 would be set to 15 dB, and $I_0$ to (65,536/(100−15))=771. Then an image pixel with OCT signal from the sample of 89 dB will be displayed with a pixel intensity of 771*(85−15)=53,970.

Figure 9A:
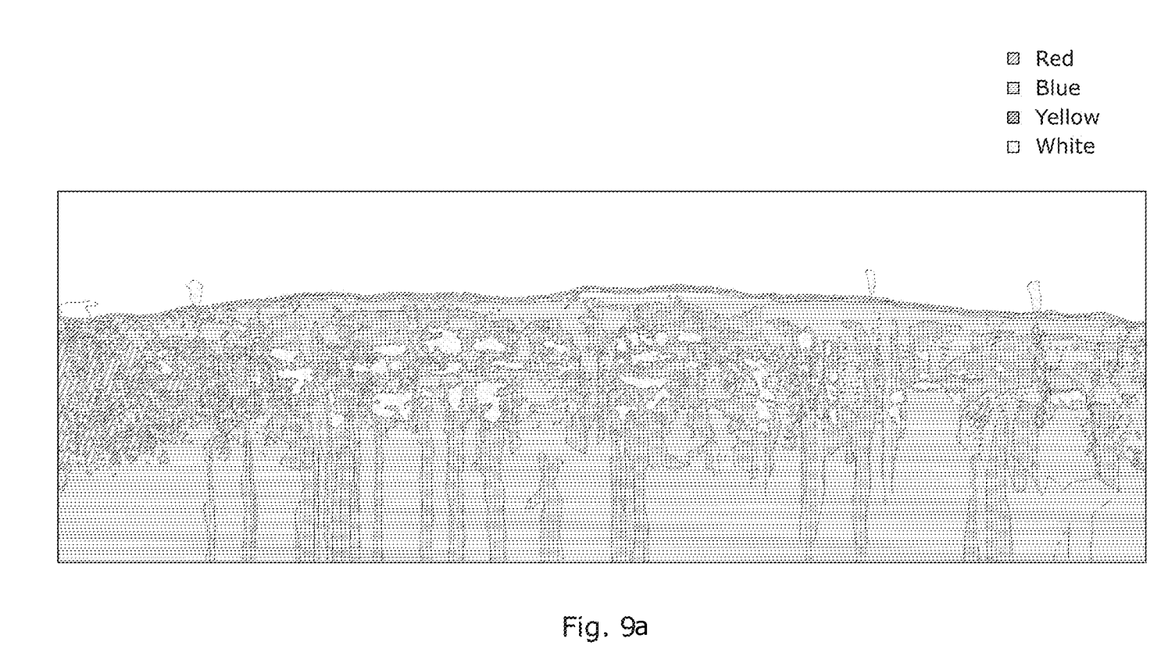
Figure 9B:
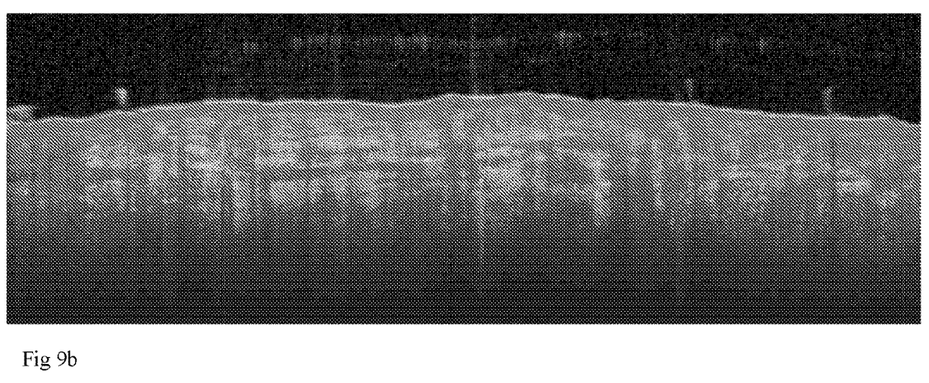

A final improvement is to apply an artificial colour scheme to the compensated filtered image, in order to further improve the visibility of clinically important features. This is done for each pixel in the image, by calculating the difference between the compensated filtered image intensity, and the fitted curve f(z) (compensated as discussed above with respect to FIGS. 10 and 11), and using this to calculate a hue, such that the hue value is proportional to this difference. The range of hues and the constant of proportionality hue/intensity difference, along with the chrominance (the degree of saturation of the colour range used), may be selected to taste and for best visual effect. FIGS. 9a and 9b of the accompanying drawings show a coloured filtered compensated image, with the colour being indicated by shading in FIG. 9a and the image being shown in greyscale in FIG. 9b.

The invention claimed is:

1. A method of processing optical coherence tomography (OCT) scans, comprising:
receiving OCT data comprising an OCT signal indicative of the level of scattering in a sample, the OCT data including the OCT signal for at least one scan through the sample, with the OCT signal having been measured at varying depth and position through the sample in each scan;
processing the OCT data for each scan with depth to produce an indicative depth scan representative of the OCT signal at each depth through all of the scans;
fitting a curve to the indicative depth scan, the curve comprising a first term which exponentially decays with respect to the depth and a second term which depends on the noise in the OCT signal; and
calculating a compensated intensity for the OCT signal at each point through each scan, the compensated intensity comprising a ratio of a term comprising a logarithm of the OCT signal to a term comprising the logarithm of the fitted curve.

2. The method of claim 1, comprising generating an image in which each pixel of the image is displayed at an intensity indicated by the compensated intensity, modified by the application of a multiplicative scale factor and an additive offset.

3. The method of claim 2, comprising displaying the image on a display.

4. The method of claim 1, comprising determining the position of the surface of the sample within each scan, and measuring the depth from the surface.

5. The method of claim 1, in which the determination of the surface of the sample comprises a detection of the surface within the scan, or by inferring the position of the surface from the arrangement of the OCT apparatus which captured the OCT scans.

6. The method of claim 4, in which the step of determining the position of the surface of the sample within each scan comprises detecting the highest point at which there is a sudden change in OCT signal intensity with depth, at each horizontal position in the scan.

7. The method of claim 6, further comprising calculating the average height of all of the points at which there is a sudden change in OCT signal.

8. The method of claim 4, comprising the step of correcting the OCT data dependent on the height of the surface of the sample in the OCT scans.

9. The method of claim 8, in which OCT data is corrected by applying an additive term which depends upon height of the surface of the sample in the OCT scans.

10. The method of claim 1, in which the first and second terms are additively combined.

11. The method of claim 10, in which the fitted curve is of the form:

$$f(z) = Ae^{-\alpha z} + N$$

where A, α and N are all constants to be determined when fitting the curve, and z is the depth through the sample.

12. The method of claim 1, in which the curve comprises a roll-off factor which varies the amount by which the compensation is reduced with increasing depth.

13. The method of claim 12, in which the compensated intensity is calculated as:

$$\text{compensated intensity} = \frac{(\log(OCT \text{ signal}) - f_\infty)}{(r + f(z) - f_\infty)}$$

where f(z) is the fitted curve and, r is the roll off factor and is a constant, and $f_\infty$ is the value of f(z) for large values of z.

14. The method of claim 2 in which image is filtered to remove graininess due to noise.

15. The method of claim 14, in which the filtering is such that a degree of filtering increases with depth.

16. The method of claim 14, in which the filtering comprises the application of at least one of a despeckle filter and a bilateral filter.

17. The method of claim 16, comprising blending the effects of the despeckle filter and the bilateral filter in a ratio that depends on depth.

18. The method of claim 2, comprising applying colour to the image.

19. The method of claim 13, in which the colour applied to a pixel depends on the difference between the compensated display intensity and the fitted curve, with the fitted curve optionally corrected by applying an additive term which depends upon height of the surface of the sample in the OCT scans.

20. The method of claim 13, in which the colour applied to each pixel has a hue which increases with increasing difference.

21. The method of claim 1, in which the sample is skin.

22. An optical coherence tomography (OCT) image processing apparatus, comprising a processor, a display coupled to the processor and storage coupled to the processor, the storage carrying program instructions which, when executed on the processor, cause it to carry out the method of claim 1.

* * * * *